United States Patent
Bikhovsky

(10) Patent No.: US 7,709,770 B2
(45) Date of Patent: May 4, 2010

(54) HEATING DEVICE FOR HEATING A PATIENT'S BODY

(75) Inventor: David Bikhovsky, Ofra (IL)

(73) Assignee: HTTP—Hypothermia Therapy Ltd., Jerusalem (IL)

( * ) Notice: Subject to any disclaimer, the term of this patent is extended or adjusted under 35 U.S.C. 154(b) by 1548 days.

(21) Appl. No.: 10/239,665

(22) PCT Filed: Mar. 28, 2001

(86) PCT No.: PCT/IL01/00288
§ 371 (c)(1), (2), (4) Date: Nov. 25, 2002

(87) PCT Pub. No.: WO01/72249
PCT Pub. Date: Oct. 4, 2001

(65) Prior Publication Data
US 2004/0026409 A1  Feb. 12, 2004

(30) Foreign Application Priority Data
Mar. 31, 2000 (GB) .................... 0007735.4

(51) Int. Cl.
H05B 3/10 (2006.01)
H05B 3/20 (2006.01)

(52) U.S. Cl. .............. 219/548; 219/209; 219/211; 219/212; 219/527; 219/528; 219/529; 219/549; 219/552; 219/545; 219/530; 219/540; 338/5; 338/210; 392/435; 392/458; 607/108; 607/109; 607/110; 607/111

(58) Field of Classification Search .......... 219/209, 219/211, 212, 527, 528, 529, 548, 549, 552, 219/545, 5, 530, 540; 338/210; 36/2.6; 398/458, 398/435; 392/435, 458; 607/96, 108–111; 5/421
See application file for complete search history.

(56) References Cited

U.S. PATENT DOCUMENTS 2,889,445 A * 6/1959 Wolf ..................... 392/435

(Continued)

FOREIGN PATENT DOCUMENTS

DE  29610436  12/1996

(Continued)

OTHER PUBLICATIONS

Derwent English Abstract of DE 29610436 dated Dec. 19, 1996.
English Abstract of EP 0110121 dated Jun. 13, 1984.
English Abstract of JP 722159 dated Jan. 24, 1995.

Primary Examiner—Shawntina Fuqua
(74) Attorney, Agent, or Firm—Ladas and Parry LLP

(57) ABSTRACT

A heating device is presented for surface heating of a body so as to maintain a required temperature of the body. The heating device comprises an electrical heating element and a power source for supplying a required voltage thereto. The heating element comprises first and second conductors, wherein the first conductor is made of a material with relatively high specific resistivity as compared to that of the second conductor, and the second conductor is made of a material with high heat conductivity. The first and second conductors are accommodated in spaced-apart parallel relationship along their lengths such that, when they are connected to the power source, electric currents flow in the conductors in opposite directions, and magnetic fields created in the vicinity of the first and second conductors are completely compensated. The first conductor thus serves as a heater and the second conductor as a heat diffuser. By accommodating the heating device such that it faces the body by the second conductor, as low as desired temperature gradient between the surface temperature of the heating conductor and the required temperature of the body can be obtained.

35 Claims, 2 Drawing Sheets

U.S. PATENT DOCUMENTS

| | | | |
|---|---|---|---|
| 3,118,042 A | 1/1964 | Parker | |
| 3,417,229 A | 12/1968 | Shomphe et al. | |
| 3,781,596 A * | 12/1973 | Galli et al. | 361/751 |
| 3,805,023 A | 4/1974 | Wainer et al. | |
| 3,882,427 A * | 5/1975 | Pflanz | 333/12 |
| 4,245,149 A | 1/1981 | Fairlie | |
| 4,532,410 A | 7/1985 | Wehmeyer | 219/211 |
| 4,665,308 A * | 5/1987 | Courvoisier et al. | 219/548 |
| 4,752,672 A | 6/1988 | Grise | |
| 4,795,998 A * | 1/1989 | Dunbar et al. | 338/5 |
| 4,908,497 A | 3/1990 | Hjortsberg | |
| 4,912,306 A | 3/1990 | Grise et al. | |
| 4,998,006 A | 3/1991 | Perlman | 219/212 |
| 5,019,797 A | 5/1991 | Marstiller et al. | |
| 5,073,688 A | 12/1991 | McCormack | |
| 5,218,185 A * | 6/1993 | Gross | 219/528 |
| 5,306,898 A * | 4/1994 | Yukawa et al. | 219/543 |
| 5,362,942 A * | 11/1994 | Vanderslice et al. | 219/209 |
| 5,403,993 A | 4/1995 | Cordia et al. | 219/549 |
| 5,422,622 A * | 6/1995 | Sakamoto | 338/210 |
| 5,495,682 A * | 3/1996 | Chen | 36/2.6 |
| 5,777,296 A * | 7/1998 | Bell | 219/211 |
| 6,111,233 A * | 8/2000 | Rock et al. | 219/545 |
| 6,153,856 A | 11/2000 | Lee | |
| 6,294,770 B1 | 9/2001 | Hasegawa et al. | |
| 6,300,597 B1 | 10/2001 | Lee | |
| 6,664,512 B2 | 12/2003 | Horey et al. | |

FOREIGN PATENT DOCUMENTS

| | | |
|---|---|---|
| EP | 0110122 | 6/1984 |
| GB | 811992 | 4/1959 |
| GB | 2104360 | 3/1983 |
| GB | 2207030 | 1/1989 |
| GB | 2316848 | 3/1998 |
| JP | 722159 | 1/1995 |
| WO | 9709866 | 3/1997 |
| WO | 9717707 | 5/1997 |
| WO | 01 23659 | 4/2001 |

* cited by examiner

HEATING DEVICE FOR HEATING A PATIENT'S BODY

FIELD OF THE INVENTION

The present invention is generally in the field of heating techniques, and relates to a heating device for surface heating of a body. The invention is particularly useful for heating a patient's body during surgical procedures and major operations.

BACKGROUND OF THE INVENTION

During a surgical procedure and within a certain time period thereafter, a patient's body requires to be externally heated. Heat transfer devices for transferring heat to the patient's body, which are used at present in operating rooms, are generally of two types: the first type utilizes a closed circuit with heated water circulating thereinside, and the second utilizes an open circuit, wherein heated air blows around the patient's body.

The heating technique of the first kind involves placing a thin rubber mattress underneath the patient. Warm water circulates through this mattress. A device, equipped with a heat exchanger and pump, warms and circulates the water. Some of these devices also have the capability of regulating the temperature of the water based on body temperature measured with a rectal probe. The heat exchange characteristics of the heating mattress are unsatisfactory since only the patient's back is warmed. It is used mainly in situations where it is impossible to place anything on the front surface of the patient's body. It is not as effective as a convection warm air system in maintaining body temperature intraoperatively.

As for the technique of the second type, it is carried out by a system consisting of a modified "hair dryer" that supplies warm air to specifically designed blankets. The blankets facilitate the distribution of the warm air over the non-operative portion of the patient's body. This system is capable of providing excellent heat transfer to a patient, and is used both to prevent the development of hypothermia and to warm hypothermic patients. The device can provide warm air at 37-42° C. The footprint of the device is small, and there is a pole mounted version. This device does not make much noise and is extremely easy to use.

Intraoperative warming is needed during most operative procedures lasting longer than 30 minutes, and in all operations on children weighing less than 15 kilograms. The only situation where warming is practically not needed, are short procedures (less than 30 minutes), and when the temperature of the patient's body is intentionally lowered. Most patients begin losing body heat either prior to anesthesia or immediately upon the induction of anesthesia. Much body heat is lost within an hour of the start of anesthesia. Therefore, warming must begin either before or immediately following the induction of anesthesia.

One of the problems of intraoperative warming is associated with the requirements for servo-controlled delivery of heat, aimed at preventing overheating and allowing for the increased delivery of warmth to patients who are continuously losing body heat. Another problem is associated with the need for the circumferential warming of limbs, warming of discontinuous areas of the body and the possibility of warming sterile areas of the operative field. It is desirable to place a heating device on individual parts of the patient's body, not underneath, so as to prevent the further loss of heat. Additionally, it is desirable to prevent the fan distribution of the warm air, and, while warming the desired parts of the patient's body to prevent the warming of surgeons, nurses and anesthesiologists presented at the time.

Notwithstanding the fact that electrical heating has evident advantages such as the possibility of the continuous control of heating, including computer control and automatic management electrical heating devices have never been used for intraoperative warming to maintain the required temperature of a patients body. This is due to the fact that the use of electrical heating in operating rooms needs to guarantee the following three complex tasks:

1. It should guarantee electrical safety, namely, to completely stave off the damage of the electrical voltage, especially taking into account that the patient is undressed, various solutions are in use during an operation, and the presence of various metal instruments, as well as hemorrhage.

2. It should guarantee to avert the danger of burns that could be caused by the local overheating of heating elements.

3. It should guarantee the absence of the influence of electromagnetic effects on electronic equipment involved in the operation or located in the vicinity of the heating device.

It is important to understand that in most cases, the above three tasks have to be accomplished together and completely. For example, to avoid the damage of electrical voltage, voltages as low as possible must be used. However, the use of low voltages with the required power compels the operation to take place with a high current, while this increase in current affects the electronics located in the vicinity of the heating device.

To decrease to zero the influence of the electromagnetic field of an electric power source onto the functioning electronics, it is known to utilize a bifilar arrangement of conductors. This technique is disclosed for example, in the patent document DE29610436. However, this technique unavoidably leads to local heating, owing to the fact that the conductors in which heat required for heating an object (e.g., a patient's body) is dissipated, are located very close to each other.

The use of bifilars is generally known as directed towards decreasing the level of the electromagnetic field. Bifilars therefore are widely used in domestic interior electric wiring, in field-effect electrical engineering, as well as in machines for contact welding where the current reaches the values of 10,000 A.

As defined by accepted standards with respect to this specific application of maintaining the temperature of a patient's body, to completely avoid the damage of burns to a patient's body, the temperature on a heating element itself, mainly on its external surface, should not exceed 41° C. At the same time, the surface temperature of the patient's body should be maintained at a level of 37° C. Accordingly, the heat flow from the heating element to the patient's body should be carried out with the maximum temperature gradient of 4° C. Taking into account that several layers of materials with very low heat conductivity (air, tissue, polyethylene) have to be accommodated between the heat dissipating element and the body, the exclusive complication of this problem is evident.

SUMMARY OF THE INVENTION

There is accordingly a need in the art to facilitate the technique of surface heating a body, by providing a novel heating device and a heating system utilizing the same.

It is a major feature of the present invention to provide such a heating device which is capable of active heat diffusion carried out by a heating element itself, so as to obtain an as low as desired temperature gradient between the temperature of the heating element and the surface temperature of a heated body and to reduce to zero a magnetic field produced by the passage of electric current through the heating element. The need for a heat diffuser is associated with the fact that in order to avoid local heating which could lead to burns, the surface through which heat is transferred to the body should be substantially equal to the surface area of the body segments to be heated. The operation of the heating element is mainly aimed at decreasing a specific heat flow that reaches the surface of the patient's body.

The main idea of the present invention consists of designing a heating element from two different conductors made of materials having, respectively, relatively lower and relatively higher specific resistivity, when compared to each other. These two different conductors are accommodated in spaced-apart parallel relationship along their length and are connected to a power source such that electric currents flow in the conductors in opposite directions, respectively. This can be implemented by simply coupling the rear end of one conductor to the front end of the other conductor to thereby form an elongated two-part element, folding the elongated element in two, and connecting the opposite ends of the elongated element (i.e., the free ends of the two conductors) to a power source.

The conductor having higher specific resistivity serves as a heating conductor, while the other conductor having lower specific resistivity is characterized by high heat conductivity and faces the body to be heated, when in the operation of the device. This conductor with relatively low resistivity and high heat conductivity serves as a heat diffuser, and is accommodated between the heating conductor and the body to be heated. Preferably, the heat diffuser has an external surface larger than that of the heating conductor, preferably no less than 5 times larger. Due to the high heat conductivity of this conductor (heat diffuser), heat dissipated by the heating conductor is uniformly distributed and transferred to the body to be heated with an acceptable density of the heat flow, namely, such as to prevent overheating of the body.

With regard to the above indicated application of maintaining the temperature of the patient's body at 37° C. when in an operating room, it has been found by the inventor that, due to the provision of a heat diffuser, it is possible to reduce the temperature of the external surface of the heating conductor at 3-4° C., while maintaining the required temperature of the surface of the patient's body.

The heating device, according to the invention, actually presents a heater with an active diffuser. When using an accumulator as a common power source for both the heating conductor and the heat diffuser conductor, it appears to be sufficient to connect the heat diffuser conductor in series with the heating conductor to completely solve the problem of the influence of the heating element onto the electronics located in its vicinity. Generally, however, each of these conductors can be associated with its own power source, preferably an accumulator.

It should be noted that the heating element may comprise an additional heat diffuser conductor. This additional heat diffuser conductors, which faces the object to be heated during the operation of the device, is the so-called "passive" diffuser and is not connected to the power source. The passive heat diffuser conductor may, for example, be located inside a bed sheet. The other heat diffuser conductor is "active", being connected to the power source. The "passive" heat diffuser conductor is in good thermal contact with the "active" heat diffuser conductor, and is in good electric insulation from the "active" heat diffuser conductor. The heating conductor and the "active" heat diffuser conductor are accommodated and connected to the power source in a manner to provide compensation of the electromagnetic fields produced by the passage of electric currents therethrough. Each of the conductors (bands) is covered by a thin insulating layer, e.g., lacquer.

The heat diffuser conductor with high heat conductivity carries out three functions: (1) it reduces the density of the heat flow that reaches the surface of the body to be heated; (2) provides uniform heat transfer to the surface area to be heated; and (3) enables complete compensation of a magnetic field created by an electric current passing through the heating strip, provided the electric currents flow in these conductors in the opposite directions.

An accumulator, when used in the heating device of the present invention, also performs two important functions: first, it provides a direct current supply source of low voltage without the need for grounding, and has no alternating component (thereby turning the task of avoiding the influence onto the electronics located in the vicinity of the heating device into the task of compensating for a magnetic field created by the electric current flowing through the heating conductor); second, it presents not only a power supply source of low, safe voltage, but safety is even guaranteed in any accidental situation arising, since when being connected to the heating device, the accumulator is previously disconnected from the power network by a mechanical switch.

The application of heating a patient's body actually presents surface heating for maintaining the surface temperature of a heated body.

There is thus provided according to one broad aspect of the present invention, a heating device for surface heating of a body so as to maintain a required temperature of the body, the heating device comprising an electrical heating element and a power source for supplying a required voltage to the heating element, wherein:

said heating element comprises first and second conductors made of materials with relatively high and low specific resistivities, respectively, as compared to each other, the second conductor material having high heat conductivity;

the first and second conductors are accommodated in spaced-apart parallel relationship along their lengths such that, when the first and second conductors are connected to the power source, electric currents flow in the first and second conductors in opposite directions, the first conductor being thereby a heater and the second conductor being a heat diffuser, thereby providing as low as desired temperature gradient between the surface temperature of the heating conductor and said required temperature of the body, when the heating element faces the body by the second conductor, and compensating magnetic fields produced in the vicinity of the heating element by the electric current flows in the first and second conductors.

The surface area of the second conductor is larger than the surface area of the first conductor. Generally, the surface area of the second conductor substantially corresponds to the surface area of the body to be heated.

Preferably, each of the first and second conductors is a strip. The first conducting strip is designed such that its physical parameters (length l, width b, thickness δ and specific resistivity ρ) are connected to electrical parameters of the power source directly coupled to the heating element in accordance with the following relationships:

$$l \geq k \cdot U \cdot \sqrt{\frac{\delta}{\rho}}$$

$$b \geq k \cdot I \cdot \sqrt{\frac{\rho}{\delta}}$$

Here, U is the voltage that falls on the first conductor; I is the current flowing through the conductor; k is a coefficient depending on the body to be heated and said required temperature, so as to satisfy the condition that electric power supplied to the conductor is substantially equal with a heat power dissipated through the surface of the conductor.

The above approach for designing a heating strip aimed at providing an as low as desired temperature gradient between the temperature of the surface of the heating strip and the required temperature of the body is developed by the inventor of the present application and disclosed in WO 97/09866. The main idea of this technique consists of considering the relationship between the physical parameters (i.e., length, width, thickness and specific resistivity) of the heating strip, and its electrical parameters (i.e., voltage and current). The physical parameters are dictated by the heating power W required for heating a specific object to a desired temperature, that is W=kS, where S is the area of the outer surface of the heating strip through which the heating power W is dissipated (i.e., product of the length l and width b of the outer surface), and k is the coefficient depending on the object to be heated and the desired temperature. The electrical parameters are dictated by electric power, W', supplied to the heating strip by a power source, that is W'=UI, wherein U is the electric potential and I is the electric current passing through the heating strip, which depends on the specific resistivity $\rho$ of the selected electric conductive material. To facilitate the understanding of this idea, let us assume that the temperature gradient needs to be reduced. For this purpose, the value of k is appropriately increased, which automatically causes the surface area S of the heating element to be increased. This, in turn, means that lower voltages should be supplied to the heating element, and this factor is used in selecting the electric conductive material with an appropriate specific resistivity.

Preferably, the first and second materials are selected such that their specific resistivities are, respectively, in the ranges 0.3-1 Ohm·mm$^2$/m (e.g., transformer steel, stainless steel) and 0.015-0.03 Ohm·mm$^2$/m (e.g., aluminum foil, copper).

The first and second conductors may be electrically connected in series to each other. Each of the first and second strips is coated with a thin insulating layer, which may be lacquer.

Preferably, the required voltage to be supplied to the heating element is substantially low, e.g., up to 12V. To this end, the power source typically comprises a step-down transformer interconnected between the power network and the heating element. The power source preferably also comprises an accumulator unit, including at least two batteries, which are selectively operable by a switching unit, so as to connect a selective one of the batteries to the heating element. When one of the batteries is in operation, the other one may be charged with a charging unit.

The device according to the invention is particularly useful for heating a patient's body undergoing treatment, e.g., an operation in an operating room. In this case, the heating element is accommodated inside a bed-sheet for covering the body to be heated, or a mattress underneath the patient's body. The heating element may be formed of several separate parts for heating selective segments of the patient's body, such as legs and/or arms.

According to another broad aspect of the present invention, there is provided a heating device for surface heating of a patient's body in an operating room, the heating device comprising an electrical heating element and a power source coupled to the heating element for supplying a required voltage thereto, wherein said heating element comprises first and second conductors made of materials with relatively high and low specific resistivities, respectively, as compared to each other, the second conductor material having high heat conductivity;

the first and second conductors are accommodated in spaced-apart parallel relationship along their lengths such that, when the first and second conductors are connected to the power source, electric currents flow in the first and second conductors in opposite directions, the first conductor being thereby a heater and the second conductor being a heat diffuser, thereby providing an as low as desired temperature gradient between the surface temperature of the heating conductor and said required temperature of the body, when the heating element faces the body by the second conductor, and compensating magnetic fields produced in the vicinity of the heating element by the electric current flows in the first and second conductors.

According to yet another aspect of the present invention, there is provided a heating system to be applied to a body for heating it up to a required temperature and maintaining this temperature, the system comprising a heating device, a power source for supplying a required voltage thereto, and a control system, wherein the heating device comprises a heating element composed of first and second conductors made of materials with relatively high and low specific resistivities, respectively, as compared to each other, the second conductor material having high heat conductivity;

the first and second conductors are accommodated in spaced-apart parallel relationship along their lengths such that, when the first and second conductors are connected to the power source, electric currents flow in the first and second conductors in opposite directions, the first conductor being thereby a heater and the second conductor being a heat diffuser, thereby providing an as low as desired temperature gradient between the surface temperature of the heating conductor and said required temperature of the body, when the heating element faces the body by the second conductor, and compensating magnetic fields produced in the vicinity of the heating element by the electric current flows in the first and second conductors; and the control system comprises at least one temperature sensor associated with the body to be heated, a processing and managing unit, and an indication unit, such as to provide continuous control of the temperature of the body and of the operation of the temperature sensor and to provide indication thereof.

According to yet another aspect of the present invention, there is provided a method for heating a body up to a required temperature and maintaining this temperature with the above-described heating device, the method comprising the steps of:

(i) accommodating the heating device in the vicinity of the body such that the heating element faces the body by the second conductor;

(ii) supplying a required voltage to the first and second conductors, thereby causing electric current flows in the first and second conductors in opposite directions, respectively;

(iii) continuously controlling the temperature of the body and selectively operating the voltage supply so as to provide an as low as desired temperature gradient between the surface temperature of the heating conductor and said required temperature of the body.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
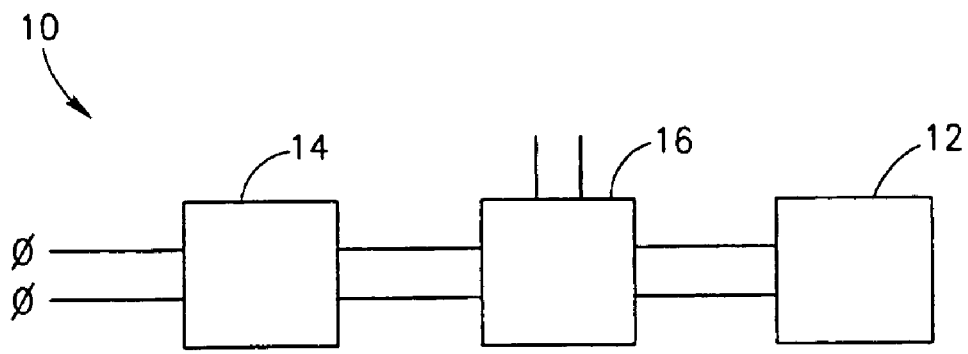
FIG. 1 is a block diagram of the main constructional parts of a system according to the invention.

Referring to FIG. 1, there is illustrated a heating system 10, according to the invention. The system 10 comprises such main constructional parts as a heating device 12 associated with a power supply source 14, and a control system 16.

The construction of the control system 16 does not form part of the present invention, and such a system may be of any known kind utilizing temperature sensors, processors, contact and non-contact switches, etc. As for the operation of the control system 16 aimed at the purposes of the present invention, it will be described further below with reference to FIG. 3. The power supply source 14 as a separate element, is also known per se, and therefore its construction and operation need not be specifically described, except to note the following: the power supply source 14 is aimed at providing the normal operational mode of the heating device in accordance with instructions generated by the control system 16, as will be described further below.

Figure 2A:
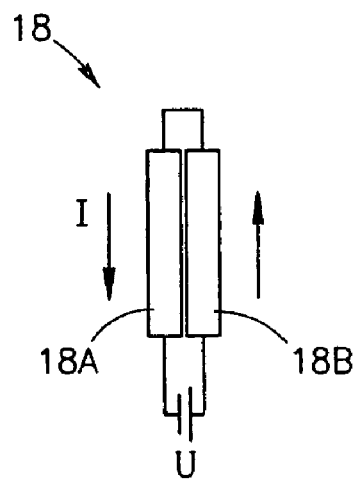
FIGS. 2A and 2B more specifically illustrate two different examples, respectively, of the relative accommodation of first and second conductors of a heating element and a power source, suitable to be used in the system of FIG. 1.
Figure 2B:
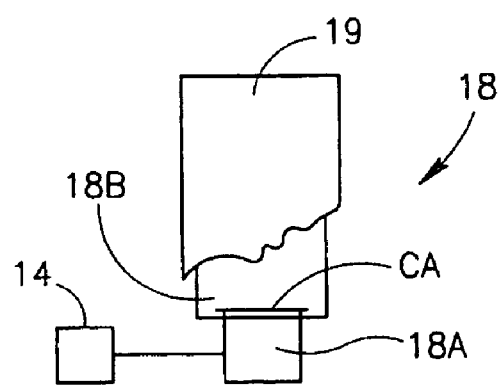

As shown in FIGS. 2A and 2B, the heating device 12 is a heating element 18 composed of two conductors 18A and 18B. The conductors 18A and 18b are made of different materials possessing different physical properties: namely, that one of the conductors (18B in the present example), which, when in operation of the device, is located between the other conductor (i.e., 18A) and the patient's body, is made of a conducting material having relatively low specific resistivity, as compared to that of the other conductor and has high heat conductivity.

For example, the conductor 18A has the specific resistivity in the range 0.3-1 Ohm·mm²/m (e.g., transformer steel or stainless steel), and the conductor 18B has the specific resistivity in the range 0.015-0.03 Ohm·mm²/m (e.g., aluminum foil). As a result, the conductor 18A serves as a heating conductor, while the conductor 18B serves as a heat diffuser. Such a heating element is therefore capable of performing active heat diffusion.

In the example of FIG. 2A, the conductors 18A and 18B are electrically connected in series with respect to the common power source 14, and are mounted in a spaced-apart parallel relationship along their entire lengths, close to each other. Such relative disposition of the conductors results in that electric currents flow in the conductors 18A and 18B in the opposite directions, and therefore provides for compensation of magnetic fields created by the current passage through the conductors. It should be noted that the conductors 18A and 18B may be coupled to separate voltage supply elements of the power source (i.e., may be installed in separate electric circuits).

Generally, the conductors are mounted with respect to each other such as to provide good thermal contact between them, namely, there are substantially no heat losses within the contact area.

More specifically, the present invention is useful for maintaining the temperature of the patient's body while in an operating room, and is therefore described below with respect to this application. To this end, although not specifically shown, the entire heating element 18 may be accommodated inside a bed-sheet for covering the patient's body or inside a mattress.

According to the example of FIG. 2B, only the heat diffuser conductor 18B is accommodated inside a bed-sheet 19, and only the heating conductor 18A is connected to the power source 14. A thermal contact between the conductors is provided within a contact area CA. In this case, no electric current flows through the conductor 18B during the operation of the heating device, and the conductor 18B serves for uniformly distributing the heat dissipated through the surface of the heating conductor 18A towards the surface area of the body to be heated (not shown), and for reducing the heat flow reaching the body.

In order to solve also the problem associated with the reduction of influence of electromagnetic effects on the electronic equipment in an operating room, both the heating conductor and the heat diffuser conductor are coupled to the power source, such that the electric current flows in the two conductors in the opposite directions (FIG. 2A). Actually, this can be achieved by forming a single elongated two-part element from the two conductors, and then folding the element in two at the boundary between the two conductors.

Figure 3:
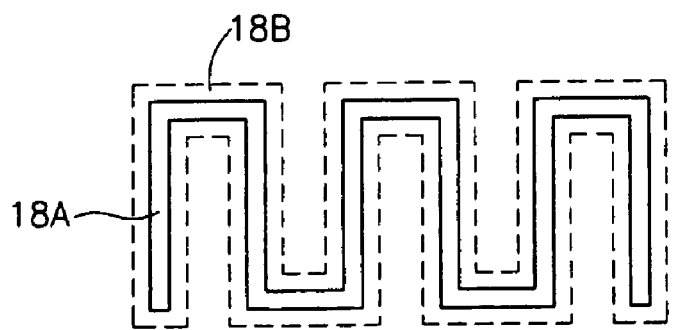
FIG. 3 illustrates an example of the implementation of the first and second conductors.

Turning now to FIG. 3, there is shown that the conductors 18A and 18B are shaped like strips, and are in the present example accommodated in a spaced-apart, parallel relationship all along their lengths. The low specific resistivity, high heat conductivity strip 18B has larger dimensions than that of the other strip 18A, such that its surface area is no less than 5 times larger than that of the strip 18A. The length and width of the heating strip 18A satisfy the following relationships:

$$l \geq k \cdot U_{heat} \cdot \sqrt{\frac{\delta}{\rho}}$$

$$b \geq k \cdot l \cdot \sqrt{\frac{\rho}{\delta}}$$

Here. $U_{heat}$ is the voltage that falls on the heating strip 18A (keeping in mind that the strips are connected in series); I is the current flowing through the entire circuit; $\rho$ is the specific resistivity of the heating strip material; $\delta$ is the thickness of the heating strip; k is a coefficient depending on the body to be heated and the required temperature, selected so as to satisfy the condition that electric power supplied to the conductor is substantially equal to a heat power dissipated through the surface of the conductor.

It should be noted, although not specifically shown, that the heating element according to the invention may include an additional heat diffuser conductor. In this case, the heating conductor and one of the heat diffuser conductors ("active" heat diffuser) are accommodated and electrically connected as exemplified in FIG. 2A, while the other heat diffuser conductor ("passive") is disconnected from the power source. This arrangement will provide complete compensation of the electromagnetic fields produced by the electric current passage through the two conductors connected to the power source, while the other heat diffuser conductor will transfer the heat dissipated by these two conductors towards the body to be heated.

As indicated above, the heating element 18 is capable of performing active heat diffusion. The requirement for heat diffusion is associated with the following. Power required for maintaining the temperature of the patient's body (mainly the temperature of his internal organs), approximately correlates with the power produced by the patient's organism in the state of rest, i.e., approximately 50 W. The average value of the entire surface of a patient is about 7000 cm$^2$. Therefore, in the simplest approximation, the supply of 0.003 W is needed for 1 cm$^2$ of the surface.

For example, if the heating strip 18A is made of stainless steel with the thickness of 0.05 mm and specific resistivity of 0.7 Ohm·mm$^2$/m, then with the current of 6 A and voltage of 2V the required temperature of the strip surface through which heat is dissipated will be about 41° C. Here, the width and length of the strip were considered, respectively, 40 mm and 1 m. In this case, the surface area of the strip through which heat is dissipated and transferred to the surface of the patient's body is 400 cm$^2$, and the heat flow from 1 cm$^2$ thereof is 0.03 W. It is thus evident that, in order to obtain a temperature of the patient's body of about 37° C., heat flow that reaches the surface of a patient's body should be reduced with respect to that generated by the heating strip 18A. This is implemented by the heat diffusing strip 18B, due to its high heat conductivity.

In the present example, the heat diffuser strip 18B is made of aluminum foil, with a thickness in the range 0.02-0.05 mm, and with the surface area larger than that of the heating strip (no less than five times). This means that if the width of the heating strip 18A is about 40 mm, then the width of the aluminum foil strip 18B is no less than 200 mm. At least those surfaces of the strips that face each other are coated with thin insulating layers, e.g., lacquer.

Due to the high heat conductivity of aluminum foil, heat dissipated by the heating strip 18A is uniformly distributed and transferred to the patient's body with the acceptable density of heat flow. Generally speaking, the density of heat flow reaching the patient's body should be such as not to cause overheating thereof above the required temperature, which is 37° C. is this specific example. As indicated above, this approach enables to reduce the temperature of surface of the heating strip by 3-4° C., while maintaining the desired temperature of the surface of the patient's body.

It should be noted that since the electric heating does not utilize liquid transfer or gaseous transfer at all, it is a simple task to divide the entire heating element into several parts of equal dimensions and equal power, taking into account that the same power is required for heating both arms of a patient and for heating his leg, in accordance with their dimensions. Therefore, each element of the heating device may be a heater with the power of 12 W, 6 W being needed for each patient's arm.

Turning back to FIG. 1, the power supply source 14 may be accumulator-based. In this case, it is sufficient to connect the aluminum strip (heat diffuser) in series with the heating strip, to solve the problem of the influence of the electric heater on electronics in the vicinity of the device.

The above can be explained as follows. First, the use of an accumulator as a power supply source eliminates the creation of an electromagnetic field, due to the absence of the alternating current component. The accumulator provides direct voltage output in which the alternating component is absent, which results in the absence of electric current oscillations, and thereby the absence of the electromagnetic field. As for a magnetic field created by the electric current passing through the heating strip, it can be reduced to zero by connecting the aluminum strip in series with the heating strip due to the mutually symmetrical accommodation of both strips and opposite directions of the currents in these strips. As the resistivity of the aluminum strip is almost by order less than that of the heating strip, owing to its smaller specific resistivity and higher width, the heat dissipated from the aluminum strip is negligible and does not affect the entire heat supply towards the patient's body.

Figure 4:
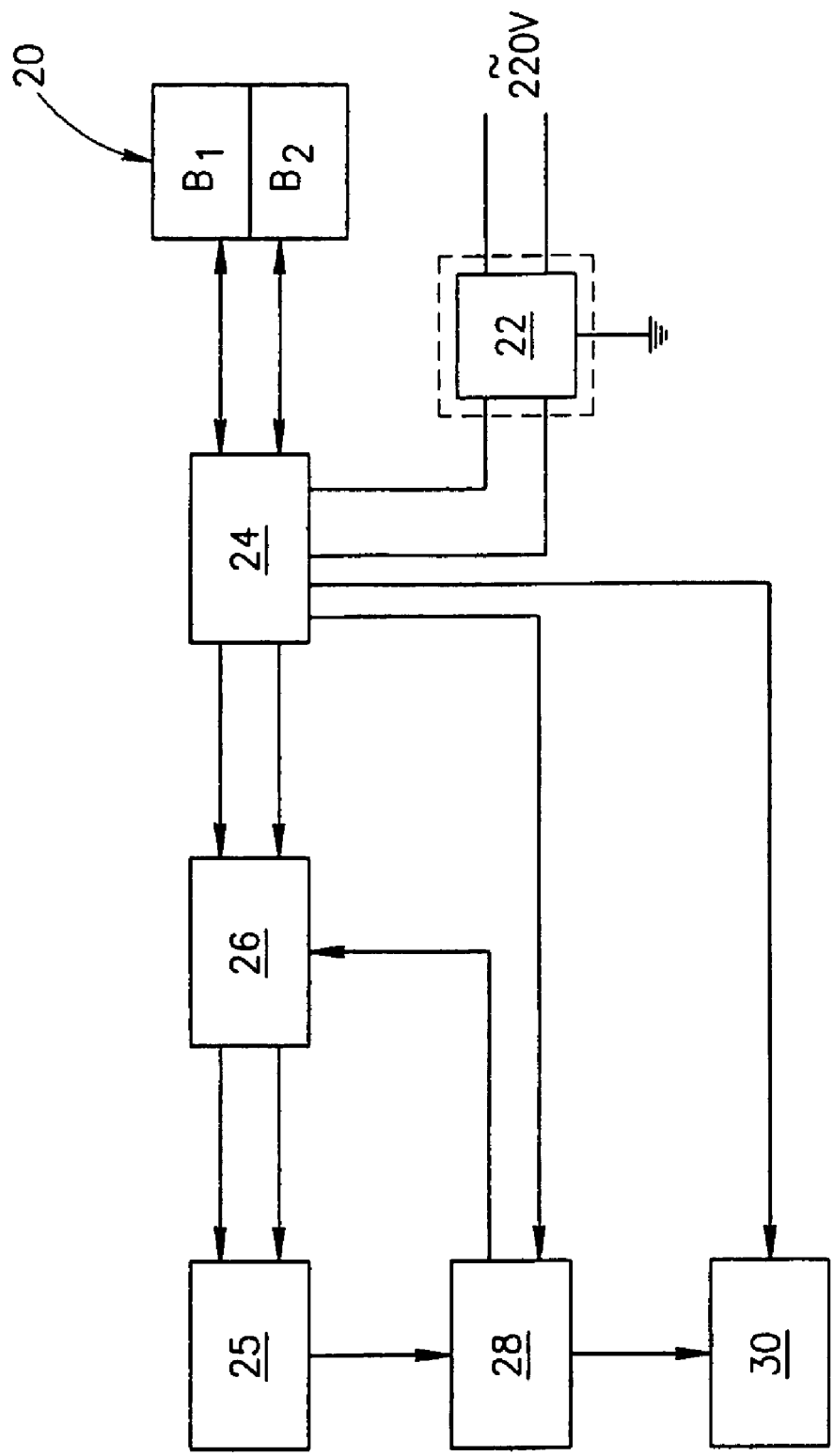
FIG. 4 is a schematic illustration of main functional components of the system of FIG. 1.

Reference is made to FIG. 4, showing the main functional elements of the system 10 of FIG. 1. The power supply source utilizes an accumulator unit 20 including two batteries $B_1$ and $B_2$, each selectively chargeable by a standard charging unit 22 typically including a step-down transformer (not shown). The charging unit 22 is interconnected between a power network and an analyzing unit 24, which operates to switch between the batteries $B_1$ and $B_2$, so as to selectively connect one of them (which is charged) to the heating element 25. A connecting unit 26 operates to connect/disconnect the heating element 25 to the accumulator unit 20. A processing and managing unit 28 is provided being interconnected between the heating element 25 and the connecting unit 26, and being connected to an indication unit 30.

The processing and managing unit 28 performs the following functions: it controls the operation of appropriately provided one or more temperature sensors (not shown) that generate data indicative of the current temperature of the patient's body; analyzes the current temperature of the patient's body; controls the operations of the switching and connecting units 24 and 26. The indication unit 30 provides indication of the operational state of the other units, and the temperature of the patient's body.

When designing the above circuit, the following important operational requirements are considered:

A. The provision of complete electrical safety for both the patient and medical personnel;

B. The continuous control of the temperature level of the patient's body;

C. The control of breaking of the temperature sensor circuit associated with means involved in the anesthesia process and with the external temperature sensors;

D. The continuous control of the extent of discharging of the battery with the possibility of switching to a reserve battery;

E. The reduction as much as possible in the signal-noise level with respect to other electronic equipment.

It should be noted that in the conventional systems of the kind specified, only the temperature of the patient's internal organs is determined. However, the temperature of the external surface of the patient's body in at least one location (but preferably 2 or 3 locations) on the body should be measured, since the disturbance of the vascular system may occur.

When putting the system of the present invention into operation by pressing an ON/OFF button (not shown), indication that the system is connected to a power network is provided by any suitable means, for example, a lamp. Other suitable indicators, e.g., lamps, provide indication that the fuses of the primary coil of the step-down transformer are in good condition. The voltage of 220V is supplied to the transformer, and the lowered alternating voltage of about 7V is provided on the secondary coil of the transformer. Alternating voltage is supplied from the secondary coil onto a diode bridge, and then onto a voltage stabilizer. As a result, an output DC voltage of about 6V is provided at the output of the charging unit 22. This voltage output is aimed at recharging the batteries, either battery $B_1$ or $B_2$, depending on the extent of the battery discharge.

As to which battery should be put in operation and which one should be recharged, this is determined by the analyzing scheme in the analyzing unit 24. During the analyzing procedure, the unit 24 generates a signal indicative of the switching procedure, in response to which a transistor (not shown) in the processing and managing unit 28 is closed, which means that the current flow in the heating strip is halted, and an electrical circuit between the units 24 and 26 is disconnected. This is implemented by mechanical means, such as relay contacts. This having been done, that battery which is more discharged among the two, is connected to the charging unit 22 by switches (relay contacts), while the other battery is connected to the circuit line operating for heating. After the completeness of the process of switching between the batteries, control signals are sequentially generated in the processing and managing unit 28, so as to put the heating device into operation, namely, the relay contacts are closed and the transistor in the unit 28 is completely opened. Then, the unit 28 is completely put in operation.

As indicated above, the presence of the temperature sensors is considered. The processing and managing unit 28 continuously controls the magnitude of the temperature and controls the situation of accidentally breaking of the temperature sensors. Concurrently with this control, the indication unit 30 proves information about the temperature value exposed to an authorized person.

Following are several processes that may occur during the operation in an operating room:

1. The temperature of the patient's body exceeds the given value. In this case, a corresponding signal is generated in the processing and managing unit 28, so as to lock the transistor. Accordingly, the relay contacts are disconnected. The indication unit 30 provides a signal indicative of the fact that the heating process is halted. The unit 28 continues to control the decrease in the temperature of the patient's body, and upon detecting that the temperature is less that the defined threshold, generates corresponding signals so as to switch on the heating process (the relay contacts are closed and the transistor is opened). The indication unit 30 provides indication to the fact that the heating is turned on.

2. The temperature of the patient's body does not reach the given value, and an indication signal indicative of switching between the batteries is generated by the unit 30. In this case, the processing and managing unit 28 generates a sequence of signals aimed at disconnecting the heating element 25 from the battery, and operates the analyzing unit 24 for switching between the batteries. The units 24 and 28 operate together so as to allow the switching process. After switching to the correct battery, the heating element is supplied with the required voltage so as to perform the heating process.

In the present example, the electrical conditions are as follows:

Electric voltage of about 220V is supplied to the accumulator unit 22 through screened wires with doubled electrical insulation. The fuses are mounted in two phases of the primary network of the transformer. Human access to the fuses without the use of a special tool is completely avoided. The transformer is of a down step torroidal kind, and the strengthened double insulation is provided between its primary and secondary windings and between the primary winding of the magnetic core. There is no such moment in time when the heating element is in its operating position during the switching between the batteries. In other words, when the processing and managing unit 28 operates to provide switching between the batteries, the heating element 25 is previously disconnected and maintained in this position during the entire re-switching process, i.e. the heating element is mechanically (and electrically) disconnected from the accumulator unit 20 and from the charging unit 22. Thus, only one, charged battery is always electrically connected to the heating element, while being at that time disconnected from the charging unit 22 (i.e., from the power network).

Thus, the present invention enables an as low as desired temperature gradient between the temperature of the surface of the heating conductor and that of a body to be heated, and complete compensation of the magnetic fields produced in the vicinity of the heating element by the electric current flows in the heating conductor and the heat diffuser conductor. The provision of the heat diffusing conductor enables to provide the uniform distribution of heat flow directed towards the body, and to reduce the heat flow reaching the body.

The thermal safety of the patient is guaranteed due to the continuous control of the temperature of the patient's body, as well as the continuous control of the state of the temperature sensors, with the provision of indication signals (audio and visual) and with necessarily disconnection of the electric heating element.

Those skilled in the art will readily appreciate that various modifications and changes can be applied to the preferred embodiment of the invention as hereinbefore exemplified without departing from its scope defined in and by the appended claims. For example, any suitable materials other than those indicated in the above description can be used for manufacturing the heating conductor and the heat diffusing conductor, provided the specific resistivity of the heat diffusing conductor is substantially lower than that of the heating conductor, while its heat conductivity is high.

What is claimed is:

1. A heating device for surface heating of a body so as to maintain a required temperature of the body, the heating device comprising an electrical heating element structure and a power source for supplying a required voltage to the heating element structure, wherein said heating element structure is constructed to enable its operation with a desired temperature of an outer surface of the heating element structure to provide as low as desired temperature gradient between the outer surface temperature of the heating element structure and the required body temperature, and substantially uniform heat transfer towards the surface of the body, the heating element structure comprising:

first and second separate elements arranged in a spaced-apart parallel relationship along their surfaces one on top of the other with an electrical insulator between them, wherein the first element is connected to the power source when the device is put in operation and serves as a heater, and the second element, which is to be located closer to the heated body, is made of a different material of a specific resistivity lower than that of the first element and has a surface area larger than that of the first element, thus operating as a heat-diffuser providing substantially uniform distribution and transfer to the body of heat created by the first element when in operation, each of said first and second elements being configured to have a predetermined length and width such that the temperature gradient between the temperature of the outer surface of the heating element structure when in operation and said required temperature of the heated body is substantially low, at least the first element being configured as a strip arranged for compensating a magnetic field created by the first conductive element when in operation.

2. The device according to claim 1, wherein the first element is made of the material with the specific resistivity at least 10 times higher than the specific resistivity of the second conductive material.

3. The device according to claim 1, wherein the surface area of the second conductive element is not less than the surface of the body to be heated.

4. The device according to claim 1, wherein each of the first and second conductive elements is shaped like a strip.

5. The device according to claim 4, wherein length, l, and width, b, of the first conductive element satisfy the following relationships:

$$l \geq k \cdot U \cdot \sqrt{\frac{\delta}{\rho}} \quad b \geq k \cdot I \cdot \sqrt{\frac{\rho}{\delta}}$$

wherein U is the voltage that falls on the first element; I is the current flowing through the first element; ρ is the specific resistivity of the first material; δ is the thickness of the first conductive strip; k is a coefficient depending on the body to be heated and said required temperature, so as to satisfy the condition that electric power supplied to the first conductive element is substantially equal to a heat power dissipated through the surface of the first conductive element.

6. The device according to claim 1, wherein each of the first and second conductive elements is coated with a thin insulating layer.

7. The device according to claim 6, wherein said thin insulating layer is lacquer.

8. The device according to claim 1, wherein said required voltage is substantially low.

9. The device according to claim 8, wherein said required voltage substantially does not exceed 12V.

10. The device according to claim 1, wherein the first material has the specific resistivity in the range 0.3-1 Ohm·mm$^2$/m.

11. The device according to claim 10, wherein said first material is transformer steel.

12. The device according to claim 10, wherein said first material is stainless steel.

13. The device according to claim 1, wherein the second material has the specific resistivity in the range 0.015-0.03 Ohm·mm$^2$/m.

14. The device according to claim 13, wherein said second material is aluminum foil.

15. The device according to claim 1, wherein said power source comprises an accumulator unit.

16. The device according to claim 15, wherein said accumulator unit comprises at least two batteries, selectively operable by a switching unit, so as to connect a selective one of the batteries to the heating element structure.

17. The device according to claim 16, wherein a charging unit is provided and selectively operable to charge that one of the batteries which is disconnected from the heating element structure.

18. The device according to claim 16, wherein said selected one of the batteries, while being connected to the heating element structure, is mechanically and electrically disconnected from a power network.

19. The device according to claim 18, intended for heating the body of a patient undergoing treatment, at least said second conductive element being accommodated inside a mattress underneath the body to be heated.

20. The device according to claim 1, intended for heating the body of a patient undergoing treatment, at least said second conductive element being accommodated inside a bedsheet for covering the body to be heated.

21. The device according claim 1, wherein the heating device comprises an additional conductive element, which faces the body to be heated when in the operative position of the device, said additional conductive element being made from a material with a lower specific resistivity, as compared to that of said first conductive element, and being disconnected from the power source, when the device is in the operation, the additional conductive element thereby serving as an additional passive heat diffuser.

22. The device according to claim 1, wherein the first and second conductive elements have shapes and dimensions such that connecting of the second element to the power source results in electric currents in the first and second conductive elements being of the same magnitudes and opposite directions, thereby compensating a magnetic field created by the electrical heating element structure when in operation.

23. The device according to claim 22, wherein the heating device comprises an additional conductive element, which faces the body to be heated when in the operative position of the device, said additional conductive element being made from a material with a lower specific resistivity, as compared to that of said first conductive element, and being disconnected from the power source, when the device is in operation, the additional conductive element thereby serving as an additional passive heat diffuser.

24. The device according to claim 22, wherein the first and second elements are electrically connected in series to each other with respect to said power source.

25. The device according to claim 1, wherein length, l, and width, b, of the first conductive element satisfy the following relations:

$$l \geq k \cdot U \cdot \sqrt{\frac{\delta}{\rho}} \quad b \geq k \cdot I \cdot \sqrt{\frac{\rho}{\delta}}$$

wherein U is the voltage that falls on the first element; I is the current flowing through the first element; ρ is the specific resistivity of the first material; δ is the thickness of the first conductive strip; k is a coefficient depending on the body to be heated and said required temperature, so as to satisfy the condition that electric power supplied to the first conductive element is substantially equal to a heat power dissipated through the surface of the first conductive element.

26. The device according to claim 1, wherein the surface area of the second element through which the heat is transferred to the body is substantially equal to the surface area of the body part to be heated.

27. The device according to claim 1 wherein the second element which serves as the heat diffuser has a surface area at least 5 times the surface area of the first element, said second element being at a distance spaced from the first element for being placed closer to the body to be heated while the first element is spaced from the second element and disposed further from the body to be heated.

28. The device according to claim 27, wherein the second element comprises a foil of low specific resistivity and the first element is in the form of a strip which has higher specific resistivity than the foil.

29. A heating system to be applied to a body for heating it up to a required temperature and maintaining this temperature, the system comprising the heating device of claim 1, and a control system, wherein the control system comprises at least one temperature sensor associated with the body to be heated, a processing and managing unit, and an indication unit, such as to provide continuous control of the temperature of the body and of the operation of the temperature sensor and to provide indication thereof.

30. The system according to claim 29, wherein the power source comprises an accumulator unit including at least two batteries, and a charging unit for selectively charging the batteries; said control system comprises an analyzing unit for analyzing the extent of discharge of each of the batteries and selectively operating the charging device to charge a respective battery; and a switching unit for disconnecting mechanically and electrically the battery to be charged from the heating element, and the charged battery connected to the heating element from the charging device.

31. A heating device for surface heating of a body so as to maintain a required temperature of the body, the heating device comprising an electrical heating element structure and a power source for supplying a required voltage to the heating element structure, wherein said heating element structure is constructed to enable its operation with a desired temperature of an outer surface of the heating element structure to provide as low as desired temperature gradient between the outer surface temperature of the heating element structure and the required body temperature, and substantially uniform heat transfer towards the surface of the body, the heating element structure comprising:

first and second separate elements arranged in a spaced-apart parallel relationship along their surfaces one on top of the other with an electrical insulator between them, wherein the first element is connected to the power source when the device is put in operation and serves as a heater, and the second element, which is to be located closer to the heated body, is made of a different material of a specific resistivity lower than that of the first element and has a surface area larger than that of the first element, thus operating as a heat-diffuser providing substantially uniform distribution and transfer to the body of heat created by the first element when in operation, each of said first and second elements being configured to have a predetermined length and width such that the temperature gradient between the temperature of the outer surface of the heating element structure when in operation and said required temperature of the heated body is substantially low, the first and second conductive elements having shapes and dimensions such that connecting of the second element to the power source results in electric currents in the first and second conductive elements being of the same magnitudes and opposite directions, thereby compensating a magnetic field created by the electrical heating element structure when in operation.

32. The device according to claim 31, wherein at least the first element is configured as a strip arranged for compensating a magnetic field created by the first conductive element when in operation.

33. A heating device for surface heating of a body so as to maintain a required temperature of the body, the heating device comprising an electrical heating element structure and a power source for supplying a required voltage to the heating element structure, wherein said heating element structure is constructed to enable its operation with a desired temperature of an outer surface of the heating element structure to provide as low as desired temperature gradient between the outer surface temperature of the heating element structure and the required body temperature, and substantially uniform heat transfer towards the surface of the body, the heating element structure comprising:

first and second separate elements arranged in a spaced-apart parallel relationship along their surfaces one on top of the other with an electrical insulator between them, wherein the first element is connected to the power source when the device is put in operation and serves as a heater, and the second element, which is to be located closer to the heated body, is made of a different material of a specific resistivity lower than that of the first element and has a surface area larger than that of the first element, thus operating as a heat-diffuser providing substantially uniform distribution and transfer to the body of heat created by the first element when in operation, each of said first and second elements being configured to have a predetermined length and width such that the temperature gradient between the temperature of the outer surface of the heating element structure when in operation and said required temperature of the heated body is substantially low, the surface area of the second element through which the heat is transferred to the body being substantially equal to the surface area of the body part to be heated.

34. The device according to claim 33, wherein at least the first element is configured as a strip arranged for compensating a magnetic field created by the first conductive element when in operation.

35. A heating device for surface heating of a body so as to maintain a required temperature of the body, the heating device comprising an electrical heating element structure and a power source for supplying a required voltage to the heating element structure, wherein said heating element structure is constructed to enable its operation with a desired temperature of an outer surface of the heating element structure to provide as low as desired temperature gradient between the outer surface temperature of the heating element structure and the required body temperature, and substantially uniform heat transfer towards the surface of the body, the heating element structure comprising:

first and second separate elements arranged in a spaced-apart parallel relationship along their surfaces one on top of the other with an electrical insulator between them, wherein the first element is connected to the power source when the device is put in operation and serves as a heater, and the second element, which is to be located closer to the heated body, is made of a different material of a specific resistivity lower than that of the first element and has a surface area larger than that of the first element, thus operating as a heat-diffuser providing substantially uniform distribution and transfer to the body of heat created by the first element when in operation, each of said first and second elements being configured to have a predetermined length and width such that the temperature gradient between the temperature of the outer surface of the heating element structure when in operation and said required temperature of the heated body is substantially low, the second element which serves as the heat diffuser has a surface area at least 5 times the surface area of the first element, said second element being at a distance spaced from the first element for being placed closer to the body to be heated while the first element is spaced from the second element and disposed further from the body to be heated.

* * * * *